United States Patent [19]

Quirk et al.

[11] Patent Number: 4,801,742

[45] Date of Patent: Jan. 31, 1989

[54] N-FORMYLATION OF AMINO CARBOXYLATES WITH ALKYL FORMATES

[75] Inventors: Jennifer M. Quirk, Highland; Charles G. Carter, Columbia; Robert J. Kupper, Mt. Airy, all of Md.

[73] Assignee: W. R. Grace & Co.-Conn., New York, N.Y.

[21] Appl. No.: 74,752

[22] Filed: Jul. 17, 1987

[51] Int. Cl.$^4$ .......................................... C07C 102/06
[52] U.S. Cl. .................................. 562/450; 548/344; 548/496; 548/532; 548/535; 562/445; 562/447; 562/557; 562/560; 562/561; 562/567; 562/564; 562/571; 562/575
[58] Field of Search ............... 562/571, 445, 450, 575, 562/447, 557, 560, 561, 567, 564; 564/132; 548/344, 496, 532, 535

[56] References Cited

U.S. PATENT DOCUMENTS

| 1,567,312 | 12/1925 | Wietzel | 564/132 |
| 1,777,777 | 10/1930 | Wietzel | 564/132 |
| 1,787,483 | 1/1931 | Lacy | 564/132 |
| 2,866,822 | 12/1958 | Siefen | 564/132 |
| 4,098,820 | 7/1978 | Couteau | 564/132 |
| 4,260,823 | 4/1981 | Casara | 562/571 |
| 4,661,510 | 4/1987 | Krantz | 562/571 |

FOREIGN PATENT DOCUMENTS

| 45-22528 | 7/1970 | Japan | 564/132 |
| 690131 | 4/1953 | United Kingdom | 564/132 |

OTHER PUBLICATIONS

Coirre, Chem. Abst. 64: 4945(e) (1965).
Coirre, Chem. Abst. 63: 13410(e) (1965).
Israel, J. Med. Chem., 29, pp. 1273-1276.
Mortimer, "Chemistry: A Conceptual Approach," pp. 546-550 (1967).
Lehninger, "Biochemistry," 2nd Ed., pp. 71-83 (1975).
Hofmann et al.; Studies on Polypeptides, XIV; J. Amer. Chem. Soc., vol. 82, p. 3727 (1960).
Gensler et al.; J. Org. Chem.; "Cinnamic Acids from Tetrahydroisoquinoline Carboxylic Acids"; vol. 21, p. 336, 1956.
King et al.; J. Chem. Soc.; "Synthesis from Phthalimido-acids"; p. 880, 1957.
Sheehan et al.; J. Am. Chem. Soc.; "The Use of N-Formylamino Acids in Peptide Synthesis"; vol. 80, p. 1154, 1958.
Pettit et al.; J. Org. Chem.; "Formylation of Aromatic Amines with Dimethylformamide"; vol. 24, p. 895, 1959.
Moffatt et al.; J. Org. Chem.; "Formylation of t-Butylamine and t-Octylamine"; vol. 27, p. 4058; 1962.
Thomas; Tetrah. Let. Chem. Abs.; "The Preparation of N-Formyl Derivatives of Amino-Acids Using N, N'-Dicyclohexylcarbodiimide"; p. 335, 1967.
Chem. Abs.; "N-Formylating Agent for Amino Acids and Cephems"; 85(1):6043t, 1975.
Kirk Othmer; Enc. Chem. Tech.; "Formic Acid and Derivatives"; vol. 11, pp. 258-260, 1980.
Chem. Abs.; "N-Formylation of Amino Acids with Chloral"; 102(11) 96080z, 1984.
Chem. Abs.; "Enzymic Coupling of N-formyl Amino Acids and/or Peptide Residues"; 103(17) 138094k, 1985.
Galat et al.; J. Am. Chem. Soc.; "The Interaction of Amides with Amines: A General Method of Acylation"; vol. 65, pp. 1566-1567, 1944.

Primary Examiner—Michael L. Shippen
Attorney, Agent, or Firm—Jill H. Krafte

[57] ABSTRACT

Formylating the amino nitrogen of an alkali metal salt of an amino carboxylic acid, by reacting the salt with an alkyl formate in an alkanol solvent. In one embodiment, the alkyl formate is added to the reaction as such; in another embodiment, the alkyl formate is formed in situ by reaction of carbon monoxide with the alkanol solvent in the presence of the alkali metal salt of the amino carboxylic acid. The process provides a new class of compounds, the alkali metal salts of N-formyl-aspartic acids.

18 Claims, No Drawings

N-FORMYLATION OF AMINO CARBOXYLATES WITH ALKYL FORMATES

BACKGROUND OF THE INVENTION

The invention relates to N-formylation of certain amino carboxylic compounds. An amino acid carboxylic alkali metal salt, e.g., the disodium salt of aspartic acid, is reacted with an alkyl formate to convert the amino group to a N-formyl group, —NH—CHO. The alkali metal salts of N-formyl-L-aspartic acid are believed novel. In one embodiment, the alkyl formate is formed in situ from carbon monoxide and an alkanol. In another embodiment, the alkyl formate is added to the reaction. With the amine group protected (by the N-formylation) the compound can then be used in conventional dipeptide synthesis or in other chemical or enzymatic reactions. The protecting formyl group may be removed by mild hydrolysis.

N-formylation of amino carboxylic acids is not new and a number of reagents have been employed to protect the amine group in this manner. However, the prior art processes are complex, expensive and/or do not provide adequate yields. For example: L-phenylalanine has been N-formylated by treating its sodium salt with chloral, Chem. Abs. 102(11):96080z. D-phenylalanine, glycine, valine and glutamic acid have been N-formylated with $HCO_2.SO_3.Na$, Chem. Abs. 85(1):6043t. Acetic anhydride has been added to amino acid in formic acid, Sheehan et al., J. Am. Chem. Soc., Vol. 80, p. 1154 (1958); Gensler et al., J. Org. Chem., Vol. 21, p. 336 (1956). Benzyl esters of amino acid derivatives can be N-formylated with formic acid in the presence of N,N'-dicyclohexylcarbodiimide, Thomas, Tetrah. Let. 335 (1967). N-formylation of t-butylamine with ethyl formate has been reported in yields of 29.4 to 84%, Moffatt et al., J. Org. Chem., Vol. 27, p. 4058 (1962).

Both primary and secondary amines react with carbon monoxide in the presence of various catalysts to yield N-formyl amines. For example, formamide is prepared commercially by one of the following two processes: (1) by direct synthesis, reacting ammonia and carbon monoxide in methanolic sodium methoxide in the presence of catalysts; or (2) by a two-stage synthesis, first reacting carbon monoxide and methanol in the presence of catalytic sodium methoxide to form methyl formate, then treating the methyl formate with liquid or gaseous ammonia, Kirk-Othmer, Enc. Chem. Tech., 3rd Ed., Vol. 11, pp. 258–60 (1980).

BRIEF DESCRIPTION OF THE INVENTION

N-formylation of amino carboxylic acids is achieved by reacting the metal salt of the amino carboxylic acid with an alkyl formate to convert the amino group to an N-formyl group. The alkyl formate may be added to the reaction or may be formed in situ. Alkali metal salts of N-formyl-aspartic acid are disclosed.

It is a primary object of this invention to disclose a simple and direct method for the N-formylation of amino carboxylic acids. It is a related object to provide a method capable of high product yield.

Another object is to provide an N-formylation process which can be conducted at ambient pressure and temperature.

DETAILED DESCRIPTION OF THE INVENTION

A novel process for N-formylating amino carboxylic acids is disclosed, as well as novel alkali metal salts of N-formyl-aspartic acid. The process comprises reacting an alkali metal salt of an amino carboxylic acid in solution in an alkanol having 1–4 carbons in the alkyl group, thereby forming an alkali metal salt of N-formyl amino carboxylic acid. There are two basic embodiments of the present invention. In one, the alkyl formate is added as such. In the other, the alkyl formate is formed in situ.

In this description, the term "amino carboxylic acid" refers to compounds that carry one or more amine groups and one or more carboxylic groups. The amino nitrogen may be a ring member. Suitable amino carboxylic compounds include those with one amino and one carboxylic group, e.g., glycine, alanine, aminobutyric acid, valine, and the like. Such compounds fall within with the genus $H_2N$—R—COOH, where R is a linear or branched alkylene with 1 to 10 carbons. Suitable compounds with one amino and one carboxylic group also include serine, threonine, phenylalanine, tyrosine, and the like. These materials carry hydroxyl and/or aromatic substituents. Compounds with one amino and two carboxylic groups are especially suitable, e.g., aminomalonic acid, L-aspartic acid, glutamic acid, and the like.

The naturally occurring amino carboxylic acids are well known: alanine, arginine, asparagine, aspartic acid, cysteine, cystine, 3,5-dibromotyrosine, 3,5-diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophan, tyrosine and valine.

The term "alkali metal" as used herein refers to lithium, sodium, potassium, cesium and rubidium. Sodium and potassium are preferred.

As used herein, "N-formylation" means that the amino nitrogen is converted to an N-formyl group by acquisition of carbonyl:

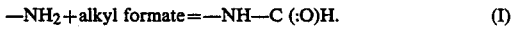
$$-NH_2 + \text{alkyl formate} = -NH-C(:O)H. \qquad (I)$$

In the case where the amine is a secondary amine, e.g., where the nitrogen is a ring nitrogen, the N-formyl group is

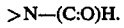
$$>N-(C:O)H.$$

Alkyl Formate Added as Such—In the first basic embodiment of this invention, an alkali metal salt of an amino carboxylic acid and a stoichiometric excess of alkyl formate are dissolved in an alkanol. The alkyl group in the formate can have 1 to 4 carbons. Methyl or ethyl formate is preferred. The alkanol can have 1–4 carbons, and is preferably methanol or ethanol. The reaction is conveniently conducted at room temperature, or the solution may be heated. Heating to temperatures up to about 40° to 75° C. (or below the boiling temperature of the alkyl formate) may be desired to speed the reaction. The reaction solution preferably is stirred. Reaction progress can be followed by NMR or other convenient analytical means. Reaction times may range from about fifteen minutes to about 20 hours. The reaction is often completed within an hour or so. Volatiles are stripped under vacuum, leaving the N-formylated salt of the amino acid. The N-formylated amino acid can be recovered by protonation with a strong acid.

The alkyl formate reacts with the alkali metal salt of the amino carboxylic acid to form the N-formyl amino carboxylate salt plus byproduct alkanol. For example, in an embodiment using disodium asparate and methyl formate, the reaction is as follows:

(II)

In this embodiment, the sodium salt of aspartic acid can be prepared by reacting two equivalents of sodium metal, sodium hydroxide, or sodium methoxide with aspartic acid in methanol. Sodium metal or sodium methoxide is preferred. Other alkali metal salts of amino carboxylic acids can be prepared in similar fashion. Potassium carbonate will be suitable, where the preparation of the potassium salt of the amino carboxylic acid is desired. It is preferred to carry out the reaction under substantially anhydrous or anhydrous conditions, as the presence of water reduces the product yield.

Alkyl Formate Formed in Situ. The reaction mechanism for the second basic embodiment of the invention involves the formation of an alkyl formate in situ, via the reaction of carbon monoxide with an alkanol in the presence of an alkali metal salt of an amino carboxylic acid. This is followed by reaction of the alkyl formate with the alkali metal salt of the amino carboxylic acid to yield the sodium salt of the N-formylated amino carboxylic acid, with regeneration of the alkanol. The alkali metal salt of the amino carboxylic acid and the alkanol (used in this embodiment as both solvent and reagent) are placed in a high pressure reactor, and carbon monoxide is pressured in, in copious stoichiometric excess. In this embodiment, the alkanol must be either methanol or ethanol. The alkali metal salts may be prepared from sodium methoxide, sodium hydroxide, potassium carbonate, sodium metal, potassium methoxide or the like.

The carbon monoxide pressure is not critical. A practical lower limit is about one atmosphere. The upper limit depends largely on the reactor characteristics. A suitable working range is about 15–1000 psig (preferably 50–250 psig), but can be considerably higher, depending on the equipment design. The reactor preferably is stirred at a temperature ranging from about room temperature to about 100° C. for about fifteen minutes to about 20 hours. As with the first described basic embodiment, simply heating the reaction mixture will make some product. When the reaction is complete, the alkanol is stripped from the reaction mixture under vacuum, leaving solid N-formylated product, which can be recovered as described above.

Alkyl formate is formed in situ by reaction of the carbon mixture with the alkanol solvent in the presence of alkali metal amino acid salt. Having thus formed the alkyl formate, the N-formylation of the amino carboxylic compound proceeds in the manner of (II) above, with regeneration of alkanol for further reaction with carbon monoxide, and so on.

Using either of the above basic embodiments, the di-alkali metal salts of dicarboxylic amino acids will be formed. If the mono salt is required, it can easily be made by treatment of the di-acid with one equivalent of base, whereupon one —COOH group is converted to the —COO—alkali metal salt. The same treatment is applicable to tri- and other poly-salts.

The alkali metal salts of N-formyl derivatives of the naturally occurring amino carboxylic acids are a particularly desirable and useful group of compounds. The acids having one or two amino groups with one or two carboxyl groups are especially desirable. In these naturally occurring acids, when there is one amino group, it is almost always in the alpha position.

In the most preferred embodiment of this invention, the amino carboxylic acid is aspartic acid. The reaction products in this embodiment, the alkali metal salts of N-formyl-aspartic acid, form a novel class of compounds. These products may be formed by either of the basic embodiments described above.

Salts of N-formylated amino carboxylic acids can be converted to the free acids with a strong mineral acid, e.g., sulfuric or phosphoric acid. Then, if desired, the N-formyl group can be returned to the amine form by mild hydrolysis. As noted above, the primary reason for N-formylating an amino carboxylic compound is to protect the amine group during subsequent dipeptide synthesis. For example, in the synthesis of aspartame from aspartic acid and phenylalanine, the amino group on the aspartic acid must be protected for best yields. There are a number of ways to accomplish such protection, but in the preferred protective system, the —NH₂ group is formylated. After the peptide synthesis, the formyl group can be removed by conventional methods, e.g., by treatment with phosphoric acid or acetyl hydrazide.

The N-formylated compounds made by this invention are thus valuable intermediates in dipeptide synthesis. These compounds may also have uses unrelated to dipeptide synthesis. For example, nicotinic acid can be synthesized from N-formyl-L-aspartate by extracts of *Clostridium butylicum*.

The following examples illustrate without limiting the invention. In Examples 1–7, alkyl formate was used directly as a reactant. In Examples 8–16, alkyl formate was formed in situ from carbon monoxide.

EXAMPLE 1

(N-Formyl Glycine, Sodium Salt)

Under a nitrogen atmosphere, 0.75 gm (10 mmol) glycine was added to a solution of 10 mmol sodium methoxide in 40 ml anhydrous methanol. The mixture was stirred until the glycine had dissolved. A solution of 3.1 ml (50 mmol) methyl formate in 10 ml methanol was then added dropwise at room temperature to the stirred solution. The reaction mixture was stirred at room temperature for 2 hours. The volatile components were removed under vacuum. Examination of the residual white solid by proton NMR showed a 75% conversion of the sodium salt of glycine to its N-formyl derivative.

EXAMPLE 2

(N-Formyl-L-Alanine, Sodium Salt)

Under a nitrogen atmosphere, 0.89 gm (10 mmol) L-alanine was added to a solution of 10 mmol sodium methoxide in 40 ml anhydrous methanol. The mixture was stirred until all of the solid had dissolved. A solution of 3.1 ml (50 mmol) methyl formate in 10 ml methanol was then added dropwise at room temperature. The reaction mixture was stirred at room temperature for 18.5 hours. The volatile components were removed under vacuum. Examination of the residual white solid by proton NMR showed complete conversion of the sodium salt of N-formyl-L-alanine.

EXAMPLE 3

(N-Formyl-L-Phenylalanine, Sodium Salt)

Under a nitrogen atmosphere, 1.65 gm (10 mmol) L-phenylalanine was added to a solution of 10 mmol sodium methoxide in 40 ml anhydrous methanol. The contents of the reaction were stirred until all of the solid had dissolved. A solution of 6.2 ml (100 mmol) methyl formate in 10 ml methanol was added dropwise. The reaction mixture was stirred at room temperature for 6 hours and the volatile components were removed under vacuum. Examination of the residual white solid by proton NMR showed complete conversion to the sodium salt of N-formyl-phenylalanine.

EXAMPLE 4

(N-Formyl-L-Tyrosine, Sodium Salt)

Under a nitrogen atmosphere, 1.81 gm (10 mmol) L-tyrosine was added to a solution of 10 mmol sodium methoxide in 40 ml anhydrous methanol. The mixture was stirred at room temperature for 25 minutes. A solution of 3.1 ml (10 mmol) methyl formate in 10 ml methanol was added dropwise to the resulting slurry. After stirring for 2 hours at room temperature, some undissolved solid remained. An additional 5.0 mmol sodium methoxide in 5 ml methanol was added. Within 20 minutes the mixture had become homogeneous. Stirring was continued for a total of 19 hours, at which point the volatile components were removed under vacuum. Examination of the residual white solid by proton NMR showed complete conversion to the sodium salt of N-formyl-L-tyrosine.

EXAMPLE 5

(N-Formyl-L-Aspartic Acid, Disodium Salt)

Under a nitrogen atmosphere, 0.27 gm (2.0 mmol) L-aspartic acid was added to a solution of 4.0 mmol sodium methoxide in anhydrous methanol. A solution of 1.25 ml (20 mmol) methyl formate in 5 ml methanol was added dropwise. The resulting reaction mixture was stirred at room temperature for 18 hours. The volatile components were removed under vacuum. Examination of the residual white solid by proton NMR showed complete conversion to the disodium salt of N-formyl-L-aspartic acid. (See NMR data, below.)

EXAMPLE 6

(N-Formyl-L-Aspartic Acid, Disodium Salt)

Under a nitrogen atmosphere, 0.27 gm (2.0 mmol) L-aspartic acid was added to a solution of 4.0 sodium ethoxide in 20 ml anhydrous ethanol. Ethyl formate, 1.6 ml (20 mmol) was added and the resulting slurry was heated to reflux for 18 hours. After cooling at room temperature, the volatile components were removed under vacuum leaving 0.4 gm of a white powder. Examination by proton NMR showed 68% conversion of the disodium salt of L-aspartic acid to its corresponding N-formyl derivative. (See NMR data, below.)

EXAMPLE 7

(N-Formyl-L-Aspartic Acid, Dipotassium Salt)

Under a nitrogen atmosphere, 0.53 gm (4.0 mmol) L-aspartic acid and 1.1 gm (8.0 mmol) potassium carbonate in 60 ml methanol were heated to reflux for 20 minutes. The resulting homogeneous solution was cooled to room temperature. Methyl formate (0.5 ml, 8.0 mmol) was added and the reaction mixture was stirred at room temperature for 18 hours. The volatile components were removed under vacuum. Examination of the residual white solid by proton NMR showed a 55% conversion of the dipotassium salt of L-aspartic acid to its N-formyl derivative. (See NMR data, below.)

EXAMPLE 8

(N-Formyl-L-Aspartic Acid, Disodium Salt)

Into a 50 ml round bottom flask was added 20 ml methanol, 0.234 gm (1.75 mmol) L-aspartic acid, and 0.19 gm (3.5 mmol) sodium methoxide. The mixture was stirred at room temperature for 2 hours, during which time all reagents went into solution. The solution was then transferred at a 125 cc high pressure reactor, pressurized with 250 psig carbon monoxide and heated with stirring to 75° C. for 18 hours. After the reaction was complete, the reaction mixture and any solids formed were transferred to a 100 ml round bottom flask. The methanol was removed by evaporation and the solid residue formed was dissolved in $D_2O$. Examination of the reaction mixture by proton NMR showed the complete conversion of the aspartic acid disodium salt to N-formyl-L-aspartic acid disodium salt. (See NMR data, below.)

EXAMPLE 9

(N-Formyl-L-Aspartic Acid, Disodium Salt)

The reaction was run as described in Example 8 except that 0.40 gm (3.0 mmol) L-aspartic acid and 0.24 gm (6.0 mmol) sodium hydroxide (instead of sodium methoxide) were used. The conversion to N-formyl-L-aspartic acid disodium salt was approximately 45% as analyzed by proton NMR. (See NMR data, below.)

EXAMPLE 10

(N-Formyl-L-Aspartic Acid, Disodium Salt)

The reaction was run as described in Example 8 except that the carbon monoxide pressure was 75 psig. The conversion of L-aspartic acid disodium salt to N-formyl-L-aspartic acid disodium salt, was quantitative as analyzed by proton NMR. (See NMR data, below.)

EXAMPLE 11

(N-Formyl-Glycine, Sodium Salt)

The reaction was run as described in Example 8 except that 0.13 gm (1.7 mmol) glycine and 0.09 gm (1.7 mmol) sodium methoxide were used. The conversion of glycine sodium salt to N-formyl glycine sodium salt was quantitative as analyzed by proton NMR. (See NMR data, below.)

EXAMPLE 12

(N-Formyl-L-Alanine, Sodium Salt)

The reaction was run as described in Example 8 except that 0.15 gm (1.7 mmol) L-alanine and 0.09 gm (1.7 mmol) sodium methoxide were used. The conversion of alanine sodium salt to N-formyl-L-alanine sodium salt, was quantitative as analyzed by proton NMR.

EXAMPLE 13

(N-Formyl-L-Tyrosine, Sodium Salt)

The reaction was run as described in Example 8 except that 0.31 gm (1.7 mmol) L-tyrosine and 0.09 gm (1.7 mmol) sodium methoxide were used. The conversion of tyrosine sodium salt to N-formyl-L-tyrosine sodium salt was 65% as analyzed by proton NMR.

EXAMPLE 14

(N-Formyl-L-Phenylalanine, Sodium Salt)

The reaction was run as described in Example 8 except that 0.29 gm (1.7 mmol) L-phenylalanine and 0.09 gm (1.7 mmol) sodium methoxide were used. The conversion of L-phenylalanine sodium salt to N-formyl-L-phenylalanine sodium salt was 60% as analyzed by proton NMR.

EXAMPLE 15

(N-Formyl-L-Aspartic Acid, Dipotassium Salt)

The reaction was run as described in Example 8 except that 0.2 gm (1.5 mmol) L-aspartic acid was used, and, instead of sodium methoxide, 0.623 gm (3.0 mmol) potassium carbonate was used. The conversion of L-aspartic acid dipotassium salt to N-formyl-L-aspartic acid dipotassium salt was 45% as analyzed by proton NMR. (See NMR data, below.)

EXAMPLE 16

(N-Formyl-L-Aspartic Acid, Monosodium Salt)

The reaction was run as described in Example 8 except that 0.345 gm (2.5 mmol) aspartic acid and 0.140 gm (2.5 mmol) sodium methoxide was used. The conversion of L-aspartic acid monosodium salt to N-formyl-L-aspartic acid monosodium salt was 95% as analyzed by proton NMR. (See NMR data, below.)

PROTON NMR OF N-FORMYL-L-ASPARTIC ACID ALKALI METAL SALTS

N-Formyl-L-Aspartic Acid Disodium Salt

Beta—$CH_2$ (2.8, m; 3.0, m)
Alpha—CH—cis isomer (4.3, dd); trans isomer (4.5, dd)
N—C(:O)H —cis isomer (7.9, s); trans isomer (8.0, s)

N-Formyl-L-Aspartic Acid Dipotassium Salt

Beta—$CH_2$ (2.8, m; 3.0, m)
Alpha—CH—cis isomer (4.3, dd); trans isomer (4.5, dd)
N—C(:O)H—cis isomer (7.9, s); trans isomer (8.0, s)

N-Formyl-L-Aspartic Acid Monosodium Salt

Beta—$CH_2$ (2.2–2.7, m)
Alpha—CH—cis isomer (4.2, dd); trans isomer (4.4, dd)
N—C(:O)H—cis isomer (7.9, s); trans isomer (8.0, s)

The chemical shifts will vary slightly (±0.2 ppm) with changes in concentration an pH.

COMPARATIVE PROTON NMR

It should be noted for purposes of comparison that the alkali metal salts can be distinguished from N-formyl-L-aspartic acid:
Beta—$CH_2$ (3.0, m)
Alpha—CH—cis isomer (4.7, dd); trans isomer (4.9, dd)
N—C(:O)H—cis isomer (8.1, s); trans isomer (8.2, s)

The alkali metal salts of N-formyl-L-aspartic acid acid can also easily be distinguished from the alkali metal salts of L-aspartic acid, e.g.:

L-Aspartic Acid Dipotassium Salt

Beta—$CH_2$ (2.15, dd; 2.3, dd)
Alpha—CH—(3.9, dd)

All of the above chemical shifts are listed as parts per million (ppm) using the sodium salt of 3-(trimethylsilyl)-1-propanesulfonic acid as an internal standard.

All samples were run in $D_2O$; m = multiplet; dd = doublet of doublets; s = singlet.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A process for N-formylating an alkali metal salt of an amino carboxylic acid in which said salt reacts with an alkyl formate having 1–4 carbons in the alkyl group, in a solvent of an alkanol having 1–4 carbons, thereby forming an alkali metal salt of N-formyl amino carboxylic acid.

2. The process of claim 1 in which said alkali metal salt is the sodium or potassium salt.

3. The process of claim 1 in which said alkali metal salt is the monosodium salt.

4. The process of claim 1 which is carried out under substantially anhydrous or anhydrous conditions.

5. The process of claim 1 wherein said alkali metal salt of an amino carboxylic acid is glycine sodium salt, thereby forming N-formyl glycine sodium salt.

6. The process of claim 1 wherein said alkali metal salt of an amino carboxylic acid is alanine sodium salt, thereby forming N-formyl alanine sodium salt.

7. The process of claim 1 wherein said alkali metal salt of an amino carboxylic acid is aspartic acid salt, thereby forming N-formyl-aspartic acid salt.

8. The process of claim 1 wherein said alkali metal salt of an amino carboxylic acid is L-aspartic acid dipotassium salt, thereby forming N-formyl-L-aspartic acid dipotassium salt.

9. The process of claim 1 wherein said alkali metal salt of an amino carboxylic acid is L-aspartic acid monosodium salt, thereby forming N-formyl-L-aspartic acid monosodium salt.

10. The process of claim 1 when said alkali metal salt of an amino carboxylic acid is L-aspartic acid disodium salt, thereby forming N-formyl-L-aspartic acid disodium salt.

11. The process of claim 1 wherein said alkali metal salt of an amino carboxylic acid is tyrosine sodium salt, thereby forming N-formyl-tyrosine sodium salt.

12. The process of claim 1 wherein said alkali metal salt of an amino carboxylic acid is phenylalanine sodium salt, thereby forming N-formyl-phenylalanine sodium salt.

13. The process of claim 1 in which the alkyl formate is formed in situ by reacting carbon monoxide with methanol or ethanol in the presence of said alkali metal salt of an amino carboxylic acid.

14. The process of claim 13 in which said alkyl formate is methyl formate, said solvent is methanol and the process is carried out in the presence of a sodium or potassium salt of the amino carboxylic acid.

15. The process of claim 13 in which the reaction pressure is about 15 to 1000 psig.

16. The process of claim 15 in which said pressure is about 50 to about 250 psig.

17. The process of claim 13 in which N-formyl-L-aspartic acid disodium salt is prepared by heating together methanol and L-aspartic acid disodium salt under carbon monoxide pressure of about 50-250 psig.

18. The process of claim 1 in which said amino carboxylic acid is an alpha-amino carboxylic acid selected from the group glycine, alanine, aminobutyric acid, valine, serine, threonine, phenylalanine, tyrosine, aminomalonic acid, aspartic acid, glutamic acid, arginine, asparagine, cysteine, cystine, 3,5-dibromotyrosine, 3,5-diiodotyrosine, glutamine, histidine, hydroxylysine, hydroxyproline, isoleucine, leucine, lysine, methionine, proline, thyroxine and tryptophan.

* * * * *